United States Patent [19]

Klemm

[11] Patent Number: Plant 6,444

[45] Date of Patent: Dec. 6, 1988

[54] CARNATION NAMED KLEKOPI

[76] Inventor: Siegfried Klemm, Hanfacker 8, D 7000 Stuttgart 50, Fed. Rep. of Germany

[21] Appl. No.: 939,362

[22] Filed: Dec. 3, 1986

[51] Int. Cl.[4] ..... A01H 5/00
[52] U.S. Cl. ..... Plt./70
[58] Field of Search ..... Plt./70

*Primary Examiner*—Robert E. Bagwill
*Attorney, Agent, or Firm*—Charles W. Rummler

[57] ABSTRACT

A new variety of carnation cultivar distinguished by the light peach coloring of its medium sized blooms which are borne singly on sturdy pedicels carried by very long, strong peduncles and by its continuous and profuse production of flowers.

1 Drawing Sheet

BACKGROUND OF THE NEW PLANT

This new carnation cultivar originated as a sport of am unpatented cultivar named "Klemaxi", this sport having been discovered by me in 1982, in a field of the variety "Klemaxi" growing in my greenhouse at Stuttgart, West Germany. The fine, light peach coloring of this flower appeared that it could have substantial merit and this led me to propagate this flower by cuttings from the parent plant which were rooted in my greenhouse at Stuttgart and grown to flowering maturity. Successive generations of this new cultivar propagated by means of cuttings have demonstrated that the novel characteristics of the first asexual reproduction of this sport hold true from generation to generation and appear to be firmly fixed.

DESCRIPTION OF THE DRAWINGS

My new carnation variety is illustrated by the accompanying full color photographic drawing, which shows the inflorescence of a flower of a fully grown plant, the color rendition being as nearly true as it is reasonably possible to obtain by means of conventional photographic procedures.

DESCRIPTION OF THE NEW PLANT

The following is a detailed description of my new carnation cultivar based upon observation of plants grown under conventional greenhouse procedures, the color designation being according to The H.C.C. Colour Chart of Robert F. Wilson issued by the British Colour Counsel in collaboration with the World Horticultural Society of London, England.

THE PLANT

Origin: Sport.
Parentage: Klemaxi (unpatented).
Classification: *Dianthus caryophyllus.*
*Commercial.*—Standard.
Form: Bush.
Height: About 150 cm. to about 170 cm.
Growth: Vigorous and upright with outstanding strength.
Branching: Normal.
Foliage:
*Quantity.*—Moderate.
*Leaf size.*—Moderate.
*Leaf shape.*—Oblong with entire margins.

*Texture.*—Smooth.
*Color.*—Upper side — Blue-green. Under side — Blue-green.

THE BUD

Size: Medium, about 20 mm. in diameter and about 40 mm. long.
Form: Generally ovoid.
Opening rate: Moderate.
Color:
*When sepals first divide.*—HCC 14/3.
*When petals begin to unfurl.*—HCC 14/3.
Sepals:
*Condition.*—Curl back.
*Number.*—About 5-6.
*Color.*—Inside — Light-green. Outside — Gray-green.
Striae: Present.
Calyx:
*Shape.*—Campanulate.
*Size.*—Moderate, about 20 mm. broad and about 25 mm. long.
*Splitting.*—The calyx does not split.
*Aspect.*—Smooth.
*Peduncle.*—Rigid and erect.
*Length.*—About 80 cm.
*Color.*—Blue-green.

THE FLOWER

Blooming habit: Continuous and profuse.
Size of bloom: Medium.
*Diameter.*—About 75 mm. to about 80 mm.
*Depth.*—About 40 mm. to about 45 mm.
Borne: Singly on strong, upright pedicels.
Shape: Flat when the bloom opens and high-centered when bloom matures.
Petalage:
*Number of petals.*—About 44 to about 50.
*Arrangement.*—Generally imbricated.
*Shape of petals.*—Fan-shaped with toothed margins.
*Color.*—Outer and inside petals — HCC 14/3, which in the summer becomes slightly pale.
*Texture.*—Soft.
*Appearance.*—Shiny.
Peduncle: Sturdy and upright.
*Length.*—About 80 cm.
*Color.*—Blue-green.

Persistence: The petals hang on and dry and the bloom stays upright.

Disease resistance: Resistant to *Fusarum oxysporum* as observed in Italy, Germany, Netherland and France.

Fragrance: None.

Lasting quality:

*On plant.*—About 15 days.

*As a cut flower.*—About 12 days.

REPRODUCTIVE ORGANS

Stamens:

*Number.*—About 12 to about 15.

*Anthers.*—Color — yellow.

*Filaments.*—Color — yellow. Length — about 10 to about 15 mm.

Pistils: About 3 in number.

*Styles.*—Length — about 20 mm. to about 40 mm. Color — white.

*Stigmas.*—Color — white.

Fruit: Fertile.

*Shape.*—Ovoid.

*Color.*—Green/Brown at maturity.

I claim:

1. A new and distinct carnation cultivar, substantially as herein shown and described, characterized by its high productivity of light peach colored flowers having fan-shaped petals, the flowers being borne singly on rigid and erect pedicels carried on a very long, sturdy upright peduncle.

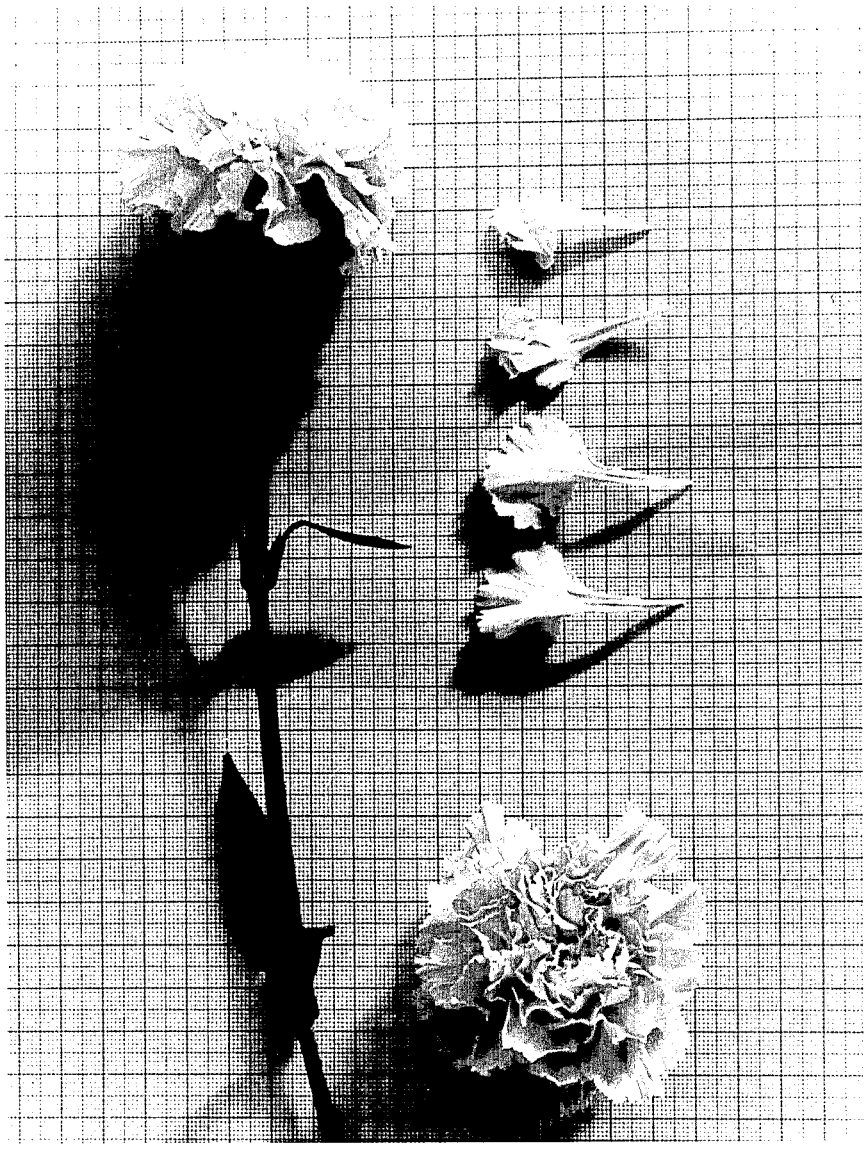

* * * * *